United States Patent [19]

Sanderson et al.

[11] Patent Number: 5,254,759
[45] Date of Patent: Oct. 19, 1993

[54] CATALYTIC REMOVAL OF PEROXIDE CONTAMINANTS FROM TERTIARY BUTYL ALCOHOL

[75] Inventors: John R. Sanderson, Leander; John F. Knifton, Austin; Melvin E. Stockton, Georgetown, all of Tex.

[73] Assignee: Texaco Chemical Company, White Plains, N.Y.

[21] Appl. No.: 897,695

[22] Filed: Jun. 12, 1992

[51] Int. Cl.$^5$ .................. C07C 29/88; C07C 31/12; C07C 29/00
[52] U.S. Cl. .................. 568/922; 568/909.8
[58] Field of Search .............. 568/922, 909.8

[56] References Cited

U.S. PATENT DOCUMENTS

| | | | |
|---|---|---|---|
| 3,624,165 | 11/1971 | Dehn et al. | 568/922 |
| 4,219,685 | 8/1980 | Savini | 568/922 |
| 4,704,482 | 11/1987 | Sanderson et al. | 568/922 |
| 4,705,903 | 11/1987 | Sanderson et al. | 568/922 |

*Primary Examiner*—Joseph E. Evans
*Attorney, Agent, or Firm*—James L. Bailey; Kenneth R. Priem; Carl G. Ries

[57] ABSTRACT

Tertiary butyl alcohol contaminated with residual amounts of peroxide contaminants such as tertiary butyl hydroperoxide, ditertiary butyl peroxide, allyl tertiary butyl peroxide, etc., (which may be prepared, for example, by catalytically reacting propylene with tertiary butyl hydroperoxide to form propylene oxide and tertiary butyl alcohol) can be effectively catalytically treated under mild conversion conditions including a temperature of about 100° to about 300° C. with a catalyst comprising ferrous oxide to substantially completely decompose the peroxide contaminants to thereby provide a treated tertiary butyl alcohol product substantially free from contaminating quantities of such peroxides.

4 Claims, No Drawings

CATALYTIC REMOVAL OF PEROXIDE CONTAMINANTS FROM TERTIARY BUTYL ALCOHOL

BACKGROUND OF THE INVENTION

1. Field of the Invention

This invention relates to a method for removing residual quantities of peroxide contaminants including tertiary butyl hydroperoxide, ditertiary butyl peroxide, allyl tertiary butyl peroxide, etc., from a tertiary butyl alcohol feedstock to provide a tertiary butyl alcohol product that is useful as an octane-enhancing component of motor fuels and also useful as a recycle stream in a continuous process for the preparation of methyl tertiary butyl ether from tertiary butyl alcohol and methanol. In accordance with the present invention, the peroxide contaminated tertiary butyl alcohol feedstock is brought into contact with a catalyst comprising ferric oxide (rust) in order to substantially selectively reduce the quantity of peroxide contaminants remaining in the tertiary butyl alcohol product.

2. Prior Art

A process for the manufacture of epoxides from olefins such as propylene is disclosed in Kollar U.S. Pat. No. 3,351,653 which teaches that the epoxide can be made by reacting an olefin with an organic hydroperoxide in the presence of an epoxidation catalyst, such as, for example, a molybdenum epoxidation catalyst. When the olefin is propylene and the hydroperoxide is tertiary butyl hydroperoxide, propylene oxide and tertiary butyl alcohol are coproducts. U.S. Pat. No. 3,350,422 teaches a similar process using a soluble vanadium catalyst. Molybdenum is the preferred catalyst. A substantial excess of olefin relative to the hydroperoxide is taught as the normal procedure for the reaction. See also U.S. Pat. No. 3,526,645 which teaches the slow addition of organic hydroperoxide to an excess of olefin as preferred.

Stein, et al. in U.S. Pat. No 3,849,451 have improved upon the Kollar process of U.S. Pat. Nos. 3,350,422 and U.S. Pat. No. 3,351,635 by requiring a close control of the reaction temperature, between 90°-200° C. and autogenous pressures, among other parameters. Stein et al. also suggests the use of several reaction vessels with a somewhat higher temperature in the last vessel to ensure more complete reaction. The primary benefits are stated to be improved yields and reduced side reactions.

It is known that isobutane can be oxidized with molecular oxygen to form a corresponding tertiary butyl hydroperoxide and that the oxidation reaction can be promoted, for example with an oxidation catalyst (see Johnston U.S. Pat. No. 3,825,605 and Worrell U.S. Pat. No. 4,296,263.

Thus, tertiary butyl alcohol can be prepared either by the direct thermal or catalytic reduction of tertiary butyl hydroperoxide to tertiary butyl alcohol or by the catalytic reaction of propylene with tertiary butyl hydroperoxide to provide propylene oxide and tertiary butyl alcohol.

It is also known that tertiary butyl alcohol can be used as an octane-enhancing component when added to a motor fuel, such as gasoline. Thus, it has heretofore been proposed, as shown, for example, by Grane U.S. Pat. No. 3,474,151 to thermally decompose tertiary butyl hydroperoxide to form tertiary butyl alcohol to be used as an octane-enhancing component of a motor fuel. Grane points out that the thermal decomposition must be conducted with care because tertiary butyl alcohol will start to dehydrate at a temperature of about 450° F. (about 232° C.) and in that dehydration becomes rapid at temperatures above about 475° F. (about 246° C.). Grane also points out that the tertiary butyl alcohol prepared in this manner will contain contaminating quantities of ditertiary butyl peroxide. Ditertiary butyl peroxide is more refractory than tertiary butyl hydroperoxide and adversely affects the octane-enhancing qualities of tertiary butyl alcohol. Grane discovered that the residual contaminating quantities of ditertiary butyl peroxide could be removed from the tertiary butyl alcohol by thermally treating the contaminated tertiary butyl alcohol at a temperature of 375° F. to 475° F. (about 190° to about 244° C.) for a time of from 1 to 10 minutes.

This concept was expanded upon by Grane et al. in U.S. Pat. Nos. 4,294,999 and 4,296,262 to provide integrated processes wherein, starting with isobutane, motor-fuel grade tertiary butyl alcohol was prepared by the oxidation of isobutane (e.g., in the presence of a solubilized molybdenum catalyst) to produce a mixture of tertiary butyl alcohol and tertiary butyl hydroperoxide from which a fraction rich in tertiary butyl hydroperoxide could be recovered by distillation. This stream, after being debutanized was subjected to thermal decomposition under pressure at a temperature of less than 300° F. (about 148.8° C.) for several hours to significantly reduce the concentration of the tertiary butyl hydroperoxide. However, the product of this thermal decomposition step still contained residual tertiary butyl hydroperoxide most of which was thereafter removed by a final thermal treatment of the contaminated tertiary butyl hydroperoxide in the manner taught by Grane U.S. Pat. No. 3,474,151.

Thus, the removal of trace quantities of tertiary butyl hydroperoxide and ditertiary butyl peroxide from motor grade tertiary butyl alcohol has received appreciable attention. Ditertiary butyl peroxide is the more refractory of the two peroxides. Another refractory peroxide that is frequently present as a contaminant is allyl tertiary butyl peroxide. Allyl tertiary butyl peroxide is more refractory than tertiary butyl hydroperoxide but less refractory than ditertiary butyl peroxide.

The problems encountered in attempting the thermal removal of contaminating quantities of peroxides such as allyl tertiary butyl peroxide and ditertiary butyl peroxide from tertiary butyl alcohol have led to the provision of a variety of catalytic processes for removing contaminating quantities of peroxides such as allyl tertiary butyl peroxide and ditertiary butyl peroxide from tertiary butyl alcohol as exemplified, for example, by Sanderson et al. U.S. Pat. No. 4,547,598, U.S. Pat. No. 4,704,482, U.S. Pat. No. 4,705,903, U.S. Pat. No. 4,742,179, U.S. Pat. No. 4,873,390, U.S. Pat. No. 4,910,349, U.S. Pat. No. 4,912,266, U.S. Pat. No. 4,912,267, U.S. Pat. No. 4,922,033, U.S. Pat. No. 4,922,034, U.S. Pat. No. 4,922,035, U.S. Pat. No. 4,922,036, etc.

In some instances, it is proposed to use silica as a support for the catalyst, e.g., Sanderson et al. U.S. Pat. No. 4,704,482, U.S. Pat. No. 4,705,903, U.S. Pat. No. 4,742,179, U.S. Pat. No. 4,873,380, etc. The silica when used as a support is normally used in an un-vitrified high surface area form, such as Kieselguhr.

SUMMARY OF THE INVENTION

The feedstocks of the present invention comprise tertiary butyl alcohol contaminated with tertiary butyl hydroperoxide, ditertiary butyl peroxide and, frequently, allyl tertiary peroxide.

When isobutane is treated to form tertiary butyl hydroperoxide, the reaction product will normally contain some tertiary butyl alcohol and other oxygenated by-products such as ditertiary butyl peroxide, allyl tertiary butyl peroxide, etc., as well as unreacted isobutane. After the unreacted isobutane is removed, a fraction composed mostly of tertiary butyl alcohol may be recovered as a distillate fraction. The tertiary butyl alcohol distillate, which will normally be contaminated with tertiary butyl hydroperoxide, ditertiary butyl peroxide, allyl tertiary peroxide, etc., may be used as a feedstock for the process of the present invention.

Tertiary butyl hydroperoxide is suitably reacted with propylene by a process of the type disclosed in Kollar U.S. Pat. No. 3,351,635 to provide an initial reaction product composed mostly of unreacted propylene, propylene oxide and tertiary butyl alcohol. However, residual quantities of tertiary butyl hydroperoxide and ditertiary butyl peroxide and other oxygenated impurities are normally present and remain dissolved in the tertiary butyl alcohol recovered from the reaction mixture. This tertiary butyl alcohol product can also be used as a feedstock for the process of the present invention.

It has been surprisingly discovered in accordance with the present invention that a feedstock comprising tertiary butyl alcohol contaminated with minor amounts of peroxide impurities such as tertiary butyl hydroperoxide, ditertiary butyl peroxide, allyl tertiary butyl peroxide, etc., can be effectively treated without significant dehydration of the tertiary butyl alcohol by bringing the peroxide-contaminated feedstock into contact with the ferric oxide catalyst in a continuous process conducted at a temperature of about 100° to about 300° C., more preferably about 160° to about 200° C., at a space velocity of about 100 to about 400 volumes of tertiary butyl alcohol feedstock per hour per volume of catalyst and a pressure of about 0 to about 2,000 psig, more preferably about 200 to about 800 psig.

Tertiary butyl alcohol obtained when propylene is reacted with tertiary butyl hydroperoxide will contain oxygenated impurities including ditertiary butyl peroxide, tertiary butyl hydroperoxide, allyl tertiary butyl peroxide, etc., and acetone. Normally, tertiary butyl alcohol prepared in this fashion will contain about 0.1 to about 5 wt. % of ditertiary butyl peroxide, about 0.0 to about 1 wt. % of tertiary butyl hydroperoxide and about 0.05 to about 2.5 wt. % of allyl tertiary butyl peroxide. Minor quantities of other peroxides and other oxygen-containing compounds such as methyl formate, etc., may also be present.

In accordance with the present invention, a tertiary butyl alcohol feedstock contaminated with peroxides such as a tertiary butyl alcohol feedstock contaminated with peroxides including about 0.1 to about 5 wt. % of ditertiary butyl peroxide, about 0.0 to about 1 wt. % of tertiary butyl hydroperoxide and about 0.05 to about 2.5 wt. % of allyl tertiary butyl peroxide, is brought into contact with a ferric oxide catalyst of the present invention under appropriate reaction conditions, such as those outlined above, to substantially selectively decompose the peroxide contaminants and thereby provide a tertiary butyl alcohol product substantially free of peroxide contaminants.

Manufacture of Methyl Tertiary Butyl Ether

Methyl tertiary butyl ether is finding increasing use as a blending component in high octane gasoline as the current gasoline additives based on lead and manganese are phased out.

Knifton U.S. Pat. No. 4,827,048 and Knifton et al. U.S. Pat. No. 4,822,921 disclose catalyst methods for the manufacture of methyl tertiary butyl ether from tertiary butyl alcohol and methanol.

The Process of the Present Invention

It has been discovered in accordance with the present invention that a peroxides-contaminated tertiary butyl alcohol recycle stream recovered from the reaction product obtained by the catalytic reaction of tertiary butyl alcohol with methanol is a suitable feedstock for use in the preparation of methyl tertiary butyl alcohol.

The results obtained with the process of the present invention are surprising and unexpected in several respects. Normally, ferric oxide, or rust, is not considered to be effective for use as a catalyst. It has been surprisingly discovered in accordance with the present invention that finely divided ferric oxide, in the form of rust, has a modest catalytic activity in respect of the decomposition of peroxides such as tertiary butyl hydroperoxide, ditertiary butyl peroxide, allyl tertiary butyl peroxide, etc., which permits effective decomposition of these impurities at temperatures below the temperature range specified in the prior art for effective thermal decomposition of the peroxide contaminants present in tertiary butyl alcohol.

The decomposition of the peroxide contaminants is substantially quantitative, conversion of the peroxides normally ranging from about 95 to about 100%. Also, there is good selectivity in that tertiary butyl alcohol is the principle decomposition product.

Thus, the provision of the process of the present invention wherein a motor-fuel grade tertiary butyl alcohol feedstock containing contaminating quantities of ditertiary butyl peroxide, tertiary butyl hydroperoxide, etc., is catalytically treated for the decomposition of the peroxides results in their substantially complete removal from the treated feedstock.

STARTING MATERIALS

The starting materials for the process of the present invention include a motor-fuel grade tertiary butyl alcohol feedstock obtained in the manner described above by the reaction of propylene with tertiary butyl hydroperoxide to form propylene oxide and tertiary butyl alcohol by the oxidation of isobutane to form tertiary butyl hydroperoxide, etc.

Tertiary butyl alcohol obtained when propylene is reacted with tertiary butyl hydroperoxide will contain oxygenated impurities including ditertiary butyl peroxide, tertiary butyl hydroperoxide, allyl tertiary butyl peroxide, etc., and acetone. Normally, tertiary butyl alcohol prepared in this fashion will contain about 0.1 to about 5 wt. % of ditertiary butyl peroxide, about 0.0 to about 1 wt. % of tertiary butyl hydroperoxide and about 0.05 to about 2.5 wt % of allyl tertiary butyl peroxide. Minor quantities of other peroxides and other oxygen-containing compounds such as methyl formate, etc., may also be present.

The catalyst compositions of the present invention comprise ferric oxide, or rust, and are easily and inexpensively prepared by using rusted iron particles such as iron filings, iron shavings, iron chips, etc. When metallic iron is exposed to air, it will react with oxygen to form ferric oxide, which will loosely adhere to the metallic iron substrate in the form of high surface area, finely divided particles. The reaction can be accelerated by immersing the particulate metallic iron in water. In accordance with one preferred embodiment of the present invention, a water-soluble transition metal compound, such as a hydroxide, acetate, acetyl acetone, etc., is dissolved in the water in which the particulate metallic iron is immersed. When this is done, the rust (i.e., ferric oxide) that is formed will also contain the corresponding transition metal oxides.

When metals, particularly iron, are exposed to air and water, they undergo corrosion. Pure iron corrodes (or rusts) slowly, while impure iron corrodes more rapidly. The reaction is slow in pure water, but rapid in solutions of electrolytes.

It has been shown that iron will not rust in dry air, nor in water which is free from dissolved oxygen. It follows that both air and water are involved in the corrosion process. The presence of an electrolyte in the water accelerates corrosion, particularly when the solution is acidic. Strained metals corrode more rapidly than unstrained ones because they are more active. Heated portions of a metal are more active than unheated ones, and corrode more rapidly. Finally, iron in contact with a less active metal such as tin, lead, or copper corrodes more rapidly than when alone, or when in contact with a more active metal such as zinc.

Corrosion can be explained by an electrochemical theory. It appears that minute primary electrochemical cells are set up when corrosion takes place. When iron is in contact with water containing an electrolyte, the half-reaction given below tends to occur.

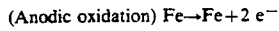
(Anodic oxidation) Fe→Fe+2 e⁻

If one portion of the iron is more active than the rest, then its tendency to go into solution is greater. This means that the active portion of the iron has a higher potential than the rest, and this portion tends to dissolve in the electrolyte. On the less active portions of the iron (lower electrode potential), hydrogen tends to form according to the half-reaction

(Cathodic reduction) 2 H+2 e⁻→H₂

The accumulation of hydrogen on the surface of iron tends to polarize the electrode and stop the cell action. However, dissolved oxygen tends to remove the hydrogen in the same manner that MnO₂ depolarizes the dry cell, and the electrochemical reaction proceeds, i.e., corrosion occurs.

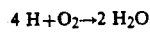
4 H+O₂→2 H₂O

Iron (II) ions combine with hydroxide ions of the electrolytic solution, forming Fe(OH)₂. Iron (II) hydroxide is then readily oxidized by air to Fe₂O₃.xH₂O, which is iron rust.

Catalytic Treatment of Tertiary Butyl Alcohol

In accordance with the present invention, a tertiary butyl alcohol feedstock, as above described, is brought into contact with a catalyst of the present invention under reaction conditions correlated to substantially selectively catalytically convert the tertiary butyl hydroperoxide, the ditertiary butyl peroxide and the allyl tertiary butyl peroxide contaminants in the tertiary butyl alcohol feedstock to decomposition products, principally tertiary butyl alcohol with not more than a minor increase in the level of contamination of any acetone, etc., that may be present in the tertiary butyl alcohol as contaminants.

The reaction should be conducted on a continuous basis by passing the tertiary butyl alcohol through a reactor containing a bed of a catalyst of the present invention under reaction conditions including a temperature within the range of about 100° to about 300° and, more preferably, at a temperature of about 160° to about 200° C. The reaction is preferably conducted at 200 to 800 psig., although pressures of about 0 to about 2000 psig. may be used if desired. The tertiary butyl alcohol should be passed over the bed of catalyst at a liquid hourly space velocity of about 0.5 to about 10.

The reaction product, after being degassed, is suitable for use as an octane-enhancing component of motor fuel, such as gasoline.

Thus, for example, the effluent from the reactor may be passed through a phase separation zone in order to permit gaseous reaction components including hydrogen and isobutane to volatilize from the product to thereby provide the desired reaction product.

The specific correlation of conditions to be utilized with any specific catalyst of the present invention can be determined by one of ordinary skill in the art with comparative ease. Thus, for example, the tertiary butyl alcohol feedstock should be analyzed prior to catalytic treatment to determine the level of contamination by tertiary butyl hydroperoxide, ditertiary butyl peroxide, acetone, methanol and isobutylene. If there is an insufficient reduction of the peroxides such that a significant amount (e.g., more than about 0.1 wt. %) of tertiary butyl hydroperoxide and/or ditertiary butyl peroxide is still present, the reaction conditions are not sufficiently severe, and should be increased such as, for example, by increasing reaction temperature or contact time in order to obtain the desired reduction of the tertiary butyl hydroperoxide.

If, on the other hand, there is a significant increase in the level of contamination of acetone, etc., the reaction conditions are too severe for the particular catalyst and the reaction conditions should be ameliorated (e.g., by reducing contact time or temperature).

WORKING EXAMPLES

A. Reactor

The reactor was a stainless steel tube (0.51"×29") 100 cc capacity which was electrically heated. Liquid feed was pumped into the bottom of the reactor. Pressure was regulated with a Skinner Uni-Flow valve and a Foxboro controller. The liquid feed was pumped with a Ruska dual drive pump.

B. Feed

The feed was a blend of 10 wt. % of water, 51 wt. % of methanol, 35 wt. % of tertiary butyl alcohol, 1.0 wt. % of methyl tertiary butyl ether and 2.5 wt. % of ditertiary butyl peroxide.

C. Catalyst Preparation (6773-78-1)

One kg Aldrich iron chips (Cat.#26,794-5) were placed in a beaker and covered with a 2 wt. % aqueous solution of sulfuric acid. Air was blown through the chips at about 200 cc/hr at ambient temperature overnight. The chips were then filtered and let stand at ambient temperature for several weeks. The chips were completely covered with a rusty-brown colored coating of ferric oxide.

D. Catalyst Preparation (6773-78-2)

About 500 g rusted iron chips from 6773-78-1 were placed in a reactor and heated to 250° C. under a nitrogen purge. Hydrogen was slowly added until the purge was 100% hydrogen. The reactor as kept at 250° C. for 4.0 hours under a flow of pure hydrogen. The reactor was then cooled to ambient temperature under nitrogen and placed in a stoppered bottle with a nitrogen pad until used. During reduction the catalyst changed from a rust brown color to black.

E. Catalyst Preparation (6773-92)

One kg Aldrich iron chips (Cat.#26,794-5) were placed in a beaker and covered with water containing 2 wt. % sulfuric acid, wt. % chromium acetylacetonate, and 1 wt. % copper acetylacetonate. Air was blown through the chips at about 200 cc/hr at ambient temperature overnight. The chips were then filtered and dried over the weekend at 100° C. The iron chips were completely covered with a rusty-brown coating of ferric oxide. Analysis by AA analysis showed more than 90 wt. % of iron, 0.05 wt. % of chromium and 0.037 wt. % of copper.

F. Thermal Decomposition

Data on the catalytic decomposition of the ditertiary butyl peroxide was generated in a plurality of runs conducted in the same reactor under reaction conditions including a pressure of 500 psig, feed rates of from 100 to 400 cc/hr, temperatures ranging from 120° to 180° C., run lengths of 4 hours and space velocities of from 1 to 4 cc of feed per hour per cc of catalyst. The data are shown in the following tables.

TABLE I

| Catalytic Decomposition of DTBP in a Continuous Reactor | | | | | |
|---|---|---|---|---|---|
| Notebook Number | 6773-16-O | 6773-79-1 | 6773-79-2 | 6773-79-3 | 6773-79-4 |
| Catalyst | | 6773-78-1 | 6773-78-1 | 6773-78-1 | 6773-78-1 |
| Reactor (cc) | | 100 | 100 | 100 | 100 |
| Pressure (psig) | | 500 | 500 | 500 | 500 |
| Feed Rate (cc/hr) | | 100 | 100 | 100 | 100 |
| Temperature (°C.) | | 120 | 140 | 160 | 180 |
| Time on Stream (hr) | | 4 | 4 | 4 | 4 |
| Space Vel. (cc/cc) | | 1.0 | 1.0 | 1.0 | 1.0 |
| DTBP Conv. (%) | | 12.8 | 38.4 | 97.8 | 99.9 |
| TBA Conversion (%) | | 0.0 | 0.o | 0.0 | 0.0 |
| Composition | | | | | |
| IC4 | 0.004 | 0.002 | 0.002 | 0.003 | 0.009 |
| MEOH/MF | 55.631 | 55.690 | 55.630 | 55.398 | 55.111 |
| Acetone | 0.000 | 0.078 | 0.343 | 1.172 | 1.522 |
| MTBE | 1.213 | 1.145 | 1.171 | 1.165 | 1.170 |
| TBA | 40.024 | 40.477 | 40.892 | 41.820 | 41.573 |
| DTBP | 2.765 | 2.411 | 1.702 | 0.062 | 0.004 |

TABLE II

| Catalytic Decomposition of DTBP in a Continuous Reactor | | | | | |
|---|---|---|---|---|---|
| Notebook Number | 6773-16-O | 6773-80-1 | 6773-80-2 | 6773-80-3 | 6773-80-4 |
| Catalyst | | 6773-78-1 | 6773-78-1 | 6773-78-1 | 6773-78-1 |
| Reactor (cc) | | 100 | 100 | 100 | 100 |
| Pressure (psig) | | 500 | 500 | 500 | 500 |
| Feed Rate (cc/hr) | | 200 | 200 | 200 | 200 |
| Temperature (°C.) | | 120 | 140 | 160 | 180 |
| Time on Stream (hr) | | 4 | 4 | 4 | 4 |
| Space Vel. (cc/cc) | | 2.0 | 2.0 | 2.0 | 2.0 |
| DTBP Conv. (%) | | 6.3 | 28.9 | 95.8 | 100.0 |
| TBA Conversion (%) | | 0.0 | 0.0 | 0.0 | 0.0 |
| Composition | | | | | |
| IC4 | 0.004 | 0.002 | 0.003 | 0.003 | 0.009 |
| MEOH/MF | 55.631 | 55.667 | 55.384 | 55.182 | 55.053 |
| Acetone | 0.000 | 0.057 | 0.592 | 1.326 | 1.922 |
| MTBE | 1.213 | 1.169 | 1.183 | 1.157 | 1.186 |
| TBA | 40.024 | 40.270 | 40.544 | 41.629 | 41.200 |
| DTBP | 2.765 | 2.591 | 1.966 | 0.115 | 0.000 |

TABLE III

| Catalytic Decomposition of DTBP in a Continuous Reactor | | | | |
|---|---|---|---|---|
| Notebook Number | 6773-16-O | 6773-81-1 | 6773-81-2 | 6773-81-4 |
| Catalyst | | 6773-78-1 | 6773-78-1 | 6773-78-1 |
| Reactor (cc) | | 100 | 100 | 100 |
| Pressure (psig) | | 500 | 500 | 500 |
| Feed Rate (cc/hr) | | 400 | 400 | 400 |
| Temperature (°C.) | | 120 | 140 | 180 |
| Time on Stream (hr) | | 4 | 4 | 4 |
| Space Vel. (cc/cc) | | 4.0 | 4.0 | 4.0 |
| DTBP conv. (%) | | 2.7 | 13.3 | 99.9 |
| TBA Conversion (%) | | 0.0 | 0.0 | 32.0 |
| Composition | | | | |
| IC4 | 0.004 | 0.002 | 0.003 | 2.160 |
| MEOH/MF | 55.631 | 55.667 | 55.812 | 54.867 |
| Acetone | 0.000 | 0.052 | 0.117 | 1.252 |
| MTBE | 1.213 | 1.172 | 1.169 | 12.797 |
| TBA | 40.024 | 40.163 | 40.270 | 27.227 |

TABLE III-continued
Catalytic Decomposition of DTBP in a Continuous Reactor

| | | | | |
|---|---|---|---|---|
| DTBP | 2.765 | 2.690 | 2.396 | 0.004 |

TABLE IV
Catalytic Decomposition of DTBP in a Continuous Reactor

| Notebook Number | 6773-16-R | 6773-93-1 | 6773-93-2 | 6773-93-3 | 6773-93-4 |
|---|---|---|---|---|---|
| Catalyst | | 6773-73-2 | 6773-73-2 | 6773-73-2 | 6773-73-2 |
| Reactor (cc) | | 100 | 100 | 100 | 100 |
| Pressure (psig) | | 500 | 500 | 500 | 500 |
| Feed Rate (cc/hr) | | 100 | 100 | 100 | 100 |
| Temperature (°C.) | | 120 | 140 | 160 | 180 |
| Time on Stream (hr) | | 4 | 4 | 4 | 4 |
| Space Vel. (cc/cc) | | 1.0 | 1.0 | 1.0 | 1.0 |
| DTBP Conv. (%) | | 40.0 | 89.4 | 99.8 | 99.8 |
| TBA Conversion (%) | | 0.0 | 8.0 | 30.3 | 39.8 |
| Composition | | | | | |
| IC4 | 0.004 | 0.070 | 0.652 | 1.623 | 0.522 |
| MEOH/MF | 55.922 | 56.177 | 54.991 | 54.478 | 56.550 |
| Acetone | 0.002 | 0.141 | 0.670 | 0.909 | 0.915 |
| MTBE | 1.218 | 1.672 | 5.782 | 13.592 | 16.318 |
| TBA | 39.901 | 40.071 | 36.692 | 27.824 | 24.008 |
| DTBP | 2.858 | 1.716 | 0.302 | 0.007 | 0.006 |

TABLE V
Catalytic Decomposition of DTBP in a Continuous Reactor

| Notebook Number | 6773-16-R | 6773-94-1 | 6773-94-2 | 6773-94-3 | 6773-94-4 |
|---|---|---|---|---|---|
| Catalyst | | 6773-78-2 | 6773-78-2 | 6773-78-2 | 6773-78-2 |
| Reactor (cc) | | 100 | 100 | 100 | 100 |
| Pressure (psig) | | 500 | 500 | 500 | 500 |
| Feed Rate (cc/hr) | | 200 | 200 | 200 | 200 |
| Temperature (°C.) | | 120 | 140 | 160 | 180 |
| Time on Stream (hr) | | 4 | 4 | 4 | 4 |
| Space Vel. (cc/cc) | | 2.0 | 2.0 | 2.0 | 2.0 |
| DTBP Conv. (%) | | 17.6 | 62.8 | 96.8 | 99.8 |
| TBA Conversion (%) | | 0.1 | 5.9 | 24.5 | 39.7 |
| Composition | | | | | |
| IC4 | 0.004 | 0.036 | 0.315 | 1.231 | 1.417 |
| MEOH/MF | 55.922 | 56.084 | 55.643 | 54.849 | 56.028 |
| Acetone | 0.002 | 0.078 | 0.384 | 0.895 | 1.174 |
| MTBE | 1.218 | 1.512 | 4.579 | 11.222 | 14.997 |
| TBA | 39.901 | 39.856 | 37.539 | 30.112 | 24.073 |
| DTBP | 2.858 | 2.355 | 1.064 | 0.091 | 0.005 |

TABLE VI
Catalytic Decomposition of DTBP in a Continuous Reactor

| Notebook Number | 6773-16-R | 6773-95-1 | 6773-95-2 | 6773-95-3 | 6773-95-4 |
|---|---|---|---|---|---|
| Catalyst | | 6773-78-2 | 6773-78-2 | 6773-78-2 | 6773-78-2 |
| Reactor (cc) | | 100 | 100 | 100 | 100 |
| Pressure (psig) | | 500 | 500 | 500 | 500 |
| Feed Rate (cc/hr) | | 400 | 400 | 400 | 400 |
| Temperature (°C.) | | 120 | 140 | 160 | 180 |
| Time on Stream (hr) | | 4 | 4 | 4 | 4 |
| Space Vel. (cc/cc) | | 4.0 | 4.0 | 4.0 | 4.0 |
| DTBP Conv. (%) | | 8.5 | 65.9 | 98.0 | 99.9 |
| TBA Conversion (%) | | 0.3 | 0.3 | 12.6 | 23.3 |
| Composition | | | | | |
| IC4 | 0.004 | 0.015 | 0.211 | 0.777 | 1.374 |
| MEOH/MF | 55.922 | 56.283 | 55.845 | 55.313 | 55.255 |
| Acetone | 0.002 | 0.040 | 0.418 | 0.806 | 1.176 |
| MTBE | 1.218 | 1.212 | 2.524 | 7.090 | 10.019 |
| TBA | 39.901 | 39.782 | 39.764 | 34.877 | 30.610 |
| DTBP | 2.858 | 2.615 | 0.974 | 0.058 | 0.004 |

| Notebook Number | 6773-16-O | 6773-81-1 | 6773-81-2 | 6773-81-4 |
|---|---|---|---|---|

TABLE VII
Catalytic Decomposition of DTBP in a Continuous Reactor

| Notebook Number | 6773-16-O | 6773-96-1 | 6773-96-2 | 6773-96-3 | 6773-96-4 |
|---|---|---|---|---|---|
| Catalyst | | 6773-92 | 6773-92 | 6773-92 | 6773-92 |
| Reactor (cc) | | 100 | 100 | 100 | 100 |
| Pressure (psig) | | 500 | 500 | 500 | 500 |
| Feed Rate (cc/hr) | | 100 | 100 | 100 | 100 |
| Temperature (°C.) | | 120 | 140 | 160 | 180 |
| Time on Stream (hr) | | 4 | 4 | 4 | 4 |
| Space Vel. (cc/cc) | | 1.0 | 1.0 | 1.0 | 1.0 |

TABLE VII-continued

Catalytic Decomposition of DTBP in a Continuous Reactor

| Notebook Number | 6773-16-O | 6773-96-1 | 6773-96-2 | 6773-96-3 | 6773-96-4 |
|---|---|---|---|---|---|
| DTBP Conv. (%) |  | 15.9 | 42.1 | 69.5 | 99.6 |
| TBA Conversion (%) |  | 0.0 | 4.5 | 6.5 | 29.4 |
| Composition |  |  |  |  |  |
| IC4 | 0.004 | 0.027 | 0.164 | 0.343 | 1.172 |
| MEOH/MF | 55.631 | 55.534 | 55.403 | 55.102 | 55.344 |
| Acetone | 0.000 | 0.046 | 0.307 | 0.642 | 1.267 |
| MTBE | 1.213 | 1.491 | 3.961 | 4.902 | 12.041 |
| TBA | 40.024 | 40.477 | 38.227 | 37.442 | 28.263 |
| DTBP | 2.765 | 2.324 | 1.600 | 0.842 | 0.010 |

TABLE VIII

Catalytic Decomposition of DTBP in a Continuous Reactor

| Notebook Number | 6773-16-O | 6773-97-1 | 6773-97-2 | 6773-97-3 | 6773-97-4 |
|---|---|---|---|---|---|
| Catalyst |  | 6773-92 | 6773-92 | 6773-92 | 6773-92 |
| Reactor (cc) |  | 100 | 100 | 100 | 100 |
| Pressure (psig) |  | 500 | 500 | 500 | 500 |
| Feed Rate (cc/hr) |  | 200 | 200 | 200 | 200 |
| Temperature (°C.) |  | 120 | 140 | 160 | 180 |
| Time on Stream (hr) |  | 4 | 4 | 4 | 4 |
| Space Vel. (cc/cc) |  | 2.0 | 2.0 | 2.0 | 2.0 |
| DTBP Conv. (%) |  | 11.9 | 54.4 | 95.7 | 99.6 |
| TBA Conversion (%) |  | 0.0 | 0.0 | 13.5 | 22.8 |
| Composition |  |  |  |  |  |
| IC4 | 0.004 | 0.018 | 0.130 | 0.626 | 0.991 |
| MEOH/MF | 55.631 | 55.736 | 55.431 | 54.634 | 54.834 |
| Acetone | 0.000 | 0.050 | 0.339 | 1.002 | 1.330 |
| MTBE | 1.213 | 1.237 | 2.351 | 7.479 | 9.834 |
| TBA | 40.024 | 40.426 | 40.284 | 34.624 | 30.896 |
| DTBP | 2.765 | 2.436 | 1.262 | 0.118 | 0.010 |

TABLE IX

Catalytic Decomposition of DTBP in a Continuous Reactor

| Notebook Number | 6773-16-O | 6773-98-1 | 6773-98-2 | 6773-98-3 | 6773-98-4 |
|---|---|---|---|---|---|
| Catalyst |  | 6773-92 | 6773-92 | 6773-92 | 6773-92 |
| Reactor (cc) |  | 100 | 100 | 100 | 100 |
| Pressure (psig) |  | 500 | 500 | 500 | 500 |
| Feed Rate (cc/hr) |  | 400 | 400 | 400 | 400 |
| Temperature (°C.) |  | 120 | 140 | 160 | 180 |
| Time on Stream (hr) |  | 4 | 4 | 4 | 4 |
| Space Vel. (cc/cc) |  | 4.0 | 4.0 | 4.0 | 4.0 |
| DTBP Conv. (%) |  | 3.5 | 51.9 | 97.2 | 99.8 |
| TBA Conversion (%) |  | 0.0 | 0.0 | 8.4 | 25.4 |
| Composition |  |  |  |  |  |
| IC4 | 0.004 | 0.004 | 0.111 | 0.690 | 0.946 |
| MEOH/MF | 55.631 | 55.844 | 55.256 | 54.848 | 54.909 |
| Acetone | 0.000 | 0.029 | 0.340 | 0.839 | 1.468 |
| MTBE | 1.213 | 1.177 | 1.801 | 6.045 | 10.765 |
| TBA | 40.024 | 40.194 | 40.932 | 36.658 | 29.871 |
| DTBP | 2.765 | 2.668 | 1.330 | 0.077 | 0.006 |

TABLE X

Catalytic Decomposition of DTBP in a Continuous Reactor

| Notebook Number | 6844-32-A | 6844-32-2 | 6844-32-3 | 6844-32-4 | 6844-32-5 |
|---|---|---|---|---|---|
| Catalyst |  | 3 mm Glass Beads | 3 mm Glass Beads | 3 mm Glass Beads | 3 mm Glass Beads |
| Reactor (cc) |  | 100 | 100 | 100 | 100 |
| Pressure (psig) |  | 500 | 500 | 500 | 500 |
| Feed Rate (cc/hr) |  | 400 | 400 | 400 | 400 |
| Temperature (°C.) |  | 120 | 140 | 160 | 180 |
| Time on Stream (hr) |  | 4 | 4 | 4 | 4 |
| Space Vel. (cc/cc) |  | 4.0 | 4.0 | 4.0 | 4.0 |
| DTBP Conv. (%) |  | 0.1 | 4.4 | 24.6 | 79.9 |
| Composition |  |  |  |  |  |
| IC4 | 0.000 | 0.003 | 0.003 | 0.006 | 0.009 |
| MEOH/MF | 0.002 | 0.018 | 0.008 | 0.010 | 0.010 |
| Acetone | 0.017 | 0.091 | 0.087 | 0.373 | 1.252 |
| MTBE | 0.238 | 0.236 | 0.230 | 0.206 | 0.167 |
| TBA | 98.342 | 98.313 | 98.334 | 98.428 | 97.989 |

TABLE X-continued

| Catalytic Decomposition of DTBP in a Continuous Reactor | | | | | |
|---|---|---|---|---|---|
| Notebook Number | 6844-32-A | 6844-32-2 | 6844-32-3 | 6844-32-4 | 6844-32-5 |
| DTBP | 0.895 | 0.894 | 0.856 | 0.675 | 0.180 |

Discussion

Tables I, II and III contain the DTBP decomposition data using the rusty iron catalyst (6773-78-1).

Tables IV, V and VI contain the DTBP decomposition data using the reduced rusty iron catalyst (6773-78-2).

Tables VII, VIII and IX contain the DTBP decomposition data using rusty iron catalyst which has chromium and copper introduced (6773-92).

Table X is a comparison example where the reactor is packed with glass beads.

The feed for Tables I through IX contains DTBP in a pseudo MTBE reactor recycle stream containing both TBA and methanol; whereas, Table X contains DIBP in almost pure TBA. A comparison of the data (rate of decomposition) is valid since solvents are not expected to have a large effect on the rate of decomposition of DTBP.

If one compares the same temperature (140° C.) and the same space velocity (4.0) for the three catalysts:

| Table | Catalyst | DTBP Conversion |
|---|---|---|
| III | Rusty Iron | 13.3 |
| VI | Partially Reduced Rusty Iron | 65.9 |
| IX | CR + Cu Rusty Iron | 51.9 |
| X | 3 mm Glass Beads | 4.4 |

Thus, rusty iron decomposes DTBP about three times faster than no catalyst (glass beads). Partially reduced iron is a very active catalyst decomposing DTBP about 15 times faster than no catalyst. Rusty iron treated with transition metal salts such as chromium and copper are also effective and catalyze the decomposition of DTBP about 12 times faster than no catalyst.

The foregoing examples are given by way of illustration only, and are not intended as limitations on the scope of this invention, as defined by the appended claims.

Having thus described our invention, what is claimed is:

1. In a method for enhancing the quality of a tertiary butyl alcohol feedstock contaminated with peroxides including ditertiary butyl peroxide, tertiary butyl hydroperoxide and allyl tertiary butyl peroxide, the improvement comprising the steps of:
   a. continuously contacting said feedstock in a peroxide decomposition reaction zone with a peroxide decomposition catalyst at a temperature of about 100° to about 300° C. for a period of time sufficient to substantially decompose said peroxide contaminants, and
   b. recovering from the products of said reaction a tertiary butyl alcohol product contaminated with not more than about 300 ppm of peroxide contaminants,
   c. said catalyst consisting essentially of finely divided ferric oxide deposited on particulate metallic iron.

2. A method as in claim 1 wherein the ferric oxide catalyst consists essentially of finely divided ferric oxide formed by exposing particulate metallic iron to oxygen to form finely divided ferric oxide in the form of rust deposited on particulate metallic iron.

3. In a method for enhancing the quality of a tertiary butyl alcohol feedstock contaminated with peroxides including about 0.1 to about 5 wt. % of ditertiary butyl peroxide, about 0.0 to about 1 wt. % of tertiary butyl hydroperoxide and about 0.05 to about 2.5 wt. % of allyl tertiary butyl peroxide, the improvement comprising the steps of:
   a. continuously contacting said feedstock in a peroxide decomposition reaction zone with a peroxide decomposition catalyst at a temperature of about 160° to 200° C., a pressure of about 0 to about 2,000 psig and a space velocity of about 100 to about 400 volumes of feedstock per hour per volume of catalyst to substantially decompose said peroxide contaminants, and
   b. recovering from the products of said reaction a tertiary butyl alcohol product contaminated with not more than about 300 ppm of peroxide contaminants,
   c. said catalyst consisting essentially of finely divided ferric oxide deposited on particulate metallic iron.

4. A method as in claim 3 wherein the ferric oxide catalyst consists essentially of finely divided ferric oxide formed by exposing particulate metallic iron to oxygen to form finely divided ferric oxide in the form of rust deposited on particulate metallic iron.

* * * * *